US00PP09513P

United States Patent [19]

Chamberlin, Sr.

[11] Patent Number: Plant 9,513

[45] Date of Patent: Apr. 23, 1996

[54] 'SEPTEMBER KING' PLUM TREE

[75] Inventor: Thomas O. Chamberlin, Sr., Visalia, Calif.

[73] Assignee: Allan A. Corrin, Reedley, Calif.

[21] Appl. No.: 410,073

[22] Filed: Mar. 24, 1995

[51] Int. Cl.[6] ..... A01H 5/00

[52] U.S. Cl. ..... Plt./38.1

[58] Field of Search ..... Plt./38.1

*Primary Examiner*—James R. Feyrer

*Attorney, Agent, or Firm*—Worrel & Worrel

[57] ABSTRACT

A new and distinct variety of plum tree which is distinguished by producing fruit which are mature for harvesting and shipment approximately September 15 to September 20 in the San Joaquin Valley of central California and wherein the fruit is large and round with a crisp and firm flesh which does not bruise easily and having a bright red skin coloration.

1 Drawing Sheet

BACKGROUND OF THE NEW VARIETY

The present invention relates to a new and distinct variety of plum tree, which will hereinafter be denominated varietally as the 'September King' plum tree, and, more particularly, to such a plum tree which produces freestone fruit, which are mature for commercial harvesting and shipment approximately September 15 to September 20 in the San Joaquin Valley of central California.

The commercial market for tree fruit, as with other fresh fruit and vegetables, is most commonly far removed geographically from the source. As world markets develop and become increasingly more dependent upon international sources of such perishable goods, the shipping and handling characteristics of varieties of fruits and vegetables become significantly more important.

Concomitantly with the development of such world markets, the sophistication and discrimination of purchasers inclreases. Fruits and vegetables which once would have been entirely acceptable in such markets, may no longer find buyers. Accordingly, the availability of world markets for fresh fruits and vegetables is dependant upon two main criteria; these being the tolerance of the varieties to shipping, handling and prolonged periods of storage and the attractiveness of the goods upon reaching market in, for example, size, shape, skin coloration and flavor. It is rare to find varieties of fresh fruits or vegetables which excel in both regards.

ORIGIN AND ASEXUAL REPRODUCTION OF THE NEW VARIETY

The plum tree of the present invention was discovered by the inventor as a chance seedling in a nursery which is located near Reedley in the San Joaquin Valley of central California. The inventor discovered the seedling from seed planted in the nursery in 1989. The first fruit of the new variety by these seedlings was observed by the inventor in the summer of 1991. As the fruit matured, it was examined as to size, shape, coloration, ripening date, flavor, texture and as to other criteria which were sought in a plum variety having the desired commercial potential. The subject seedling was selected as a candidate possessing unusual potiential.

Budwood was collected from this seedling in the winter of 1991 and 1992. Seedlings were first grafted to the new variety in the early spring of 1992. The first fruit was seen on the asexually reproduced trees of the new variety in September of 1993 and was again observed in 1994. These trees of the new variety has a very light crop in 1993 and a very heavy crop in 1994. The harvest time for th asexually reproduced trees was about mid-September and thus about the same as the parent seedling. They produced the same large, round fruit with flesh of a firm texture. The flavor of the fruit was very good. The skin coloration of the fruit was the same dark red and the leaves matched those of the parent seedling. The inventor has confirmed that the asexually reproduced trees of the new variety are the same in all respects as the parent seedling.

SUMMARY OF THE NEW VARIETY

The 'September King' plum tree is characterized by producing a freestone fruit which have a bright red skin coloration and are ripe for commercial harvesting and shipment approximately September 15 to September 20 in the San Joaquin Valley of central California. The fruit of the new variety are large in size, fully round in shape and possess and excellent flavor. Furthermore, the fruit has been determined to have outstanding storage life retaining firm flesh of very good flavor even after thirty (30) days in cold storage.

BRIEF DESCRIPTION OF THE DRAWING

The drawing is a color photograph showing mature fruit of the new variety including a first in side elevation, a second in bottom plan view showing the apex area thereof, a third in top plan view showing the base thereof, a fourth in side elevation showing the suture thereof, and a fifth sectioned and laid open to show the stone in one section and the stone cavity in the other section; and representative foliage, all of the new variety.

DETAILED DESCRIPTION

Referring more specifically to the pomological details of this new and distinct varity of plum tree, the following has been observed under the ecological conditions prevailing at the orchard of origin which is located near Reedley, Calif. All major color code designations are by reference to the *Inter-Society Color Council, National Bureau of Standards.* Common color names are also occasionally employed.

TREE:

Generally

*Size.*—Normal with upright growth.

*Vigor.*—Vigorous.

*Chilling requirements.*—Four hundred to six hundred hours.

*Figure.*—Normal.
*Productivity.*—Very good.
*Regularity of Bearing.*—Will bear well every year. This variety seems to be self fruiting, like most other plum trees. It is believed to be best planted with other plum trees to ensure good fruiting every year.

Trunk:
*Size.*—Normal, depending on pruning and shaping.
*Surface texture.*—Normal rough bark.
*Color.*—Gray-brown (63 D. gr. Br) bark.
*Lenticels — Numbers.*—Approximately 16 to 20 per square inch.
*Lenticels.*—Has long cracks in bark color (70 L.O.Y.).

Branches:
*Size.*—Normal, depending on pruning and shaping.
*Surface texture.*—Normal. Same as trunk.
*Color* — Gray-brown (16 D. gr. Br).
*Color* — One year or older wood.—Same.
*Color*—Immature branches.—Same.
*Surface texture.*—Immature growth— Smooth.
*Lenticels — Numbers.*—Approximately 16 to 20 per square inch.
*Lenticels — Size.*—Very small.

LEAVES

Size:
*Generally.*—Medium.
*Average length.*—5.72 cm (2¼ inches) to 8.26 cm (3¼ inches).
*Average Width.*—2.70 cm (1 1/16 inches) to 3.81 cm (1½ inches).

Form: Lanceolate.

Color:
*Upwardly disposed surface.*—Dark green (127 gy Ol. G).
*Downwardly disposed surface.*—Pale green (122 gy y. G).

Marginal form:
*Generally.*—Very finely serrate.

Glandular Characteristics: No glands found on stem.

Petiole:
*Size.*—Normal.
*Length.*—0.794 cm (5/16 inch).
*Width.*—0.160 cm (1/16 inch).

Stem Glands:
*Form.*—None found.

Stipules: Not found on every leaf node. When found, will be one pair.
*Size.*—Some are as long as 1.27 cm (½ inch).
*Width.*—Very fine.
*Color.*—Medium green (120 m. y. G).

FLOWERS

Flower buds: Information was taken as white started to show as apex of bud.
*Size.*—Length — 0.476 cm (3/16 inch).
*Diameter.*—0.318 cm (⅛ inch).
*Surface texture.*—Smooth.
*Shape.*—Slightly elongated.
*Petiole.*—Length — 0.476 cm (3/16 inch).
*Other characteristics.*—Buds develop on fruit spurs.
*Color.*—Light green (119 l. y. G) with white starting to show at apex of bud.

Flowers:
*Generally.*—Round in appearance.

Date of bloom: Approximately February 28 to March 4 at Reedley, Calif.

Size:
*Petal — Length.*—0.476 cm (3/16 inch).
*Petal — Diameter.*—0.476 cm (3/16 inch).

Shape: Each petal very small and round in appearance.

Petals:
*Color.*—White (263 white).

Petiole:
*Length.*—0.794 cm (5/16 inch) when in full blossom.

FRUIT

Maturity when described: Ripe for commercial harvesting and shipment approximately September 15 to September 20 near Reedley in the central San Joaquin Valley of California.

Size:
*Generally.*—Large.
*Average diameter.*—6.19 cm (2 7/16 inches) to 6.99 cm (2¾ inches).

Form:
*Uniformity.*—Good.
*Symmetry.*—Almost full round in appearance. Rounded apex area and base.

Suture:
*Generally.*—Very slightly recessed.
*Length.*—8.89 cm (3½ inches) to 9.53 cm (3¾ inches) from stem cavity to pistol point area.

Ventral surface:
*Generally.*—Rounded.

Stem cavity:
*Generally.*—Rounded.
*Width.*—0.794 cm (5/15 inch).
*Depth.*—0.953 cm (⅜0 inch).
*Base.*—Rounded.
*Apex.*—Rounded. No apex point showing.

Pistol point: Rounded to very slightly receded.

Stem:
*Generally.*—Normal.
*Length.*—1.27 cm (½ inch).
*Width.*—0.238 cm (3/32 inch).

Pistil point:
*Character.*—Smooth.

Skin:
*Thickness.*—Approximately 0.040 cm (1/64 inch) or less.
*Texture.*—Very smooth. Takes very high shine.
*Tendency to crack.*—None.
*Color.*—Dark red (260 V. dp. R) to bright red (14 V. deep. Red), with very small yellow (17 m. OY) spots which are approximately 0.159 cm (1/16 inch) and smaller.

Flesh:
*Flesh color.*—Yellow (70 l. OY) with bright red (13 deep red) next to skin.
*Surface of pit cavity.*—Quite smooth.
*Color of pit well.*—Darker yellow (72 d. OY).
*Juice production.*—Medium juicy.
*Flavor.*—Mild and sweet.
*Aroma.*—Slight.
*Texture.*—Smooth, juicy and crisp at picking time.
*Fibers.*—Numbers — none.
*Ripening.*—Even.
*Eating Quality.*—Very good. Mild to sweet and quite crisp at harvest time.

Stone:
*Attachment.*—Freestone.

*Fibers.*—Number — none.
*Size — Length.*—1.91 cm (¾ inch).
*Size — width.*—0.175 cm (11/16 inch).
*Size — thickness.*—1.11 cm (7/16 inch).
*Form.*—Generally — Elongated and almost flat in appearance.
*Apex.*—Shape — Rounded.
*Color.*—Dark yellow (72 d. OY).
*Base.*—Shape — Very small and round.
*Sides.*—Generally — Rough.
*Ridges.*—None.
*Tendency to split.*—None.

Use: Fresh market.

Keeping quality: Very good. Has been kept in cold storage for over 30 days and was still firm and had not lost its flavor.

Resistance to disease: No disease noted to date.

Harvesting: Fruit is very firm at harvest time.

Shipping and handling qualities: Does not bruise easily. Should handle and ship very well.

Although the new variety of plum tree possesses the described characteristics noted above as a result of the growing conditions prevailing near in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of plum tree, what I claim as new and desire to be secured by Plant Letters Patent is:

1. A new and distinct variety of plum tree substantially as illustrated and described which is distinguished by producing large, fully rounded fruit having a bright red skin coloration and which are mature for commercial harvesting and shipment approximately September 15 to September 20 in the San Joaquin Valley of central California.

* * * * *

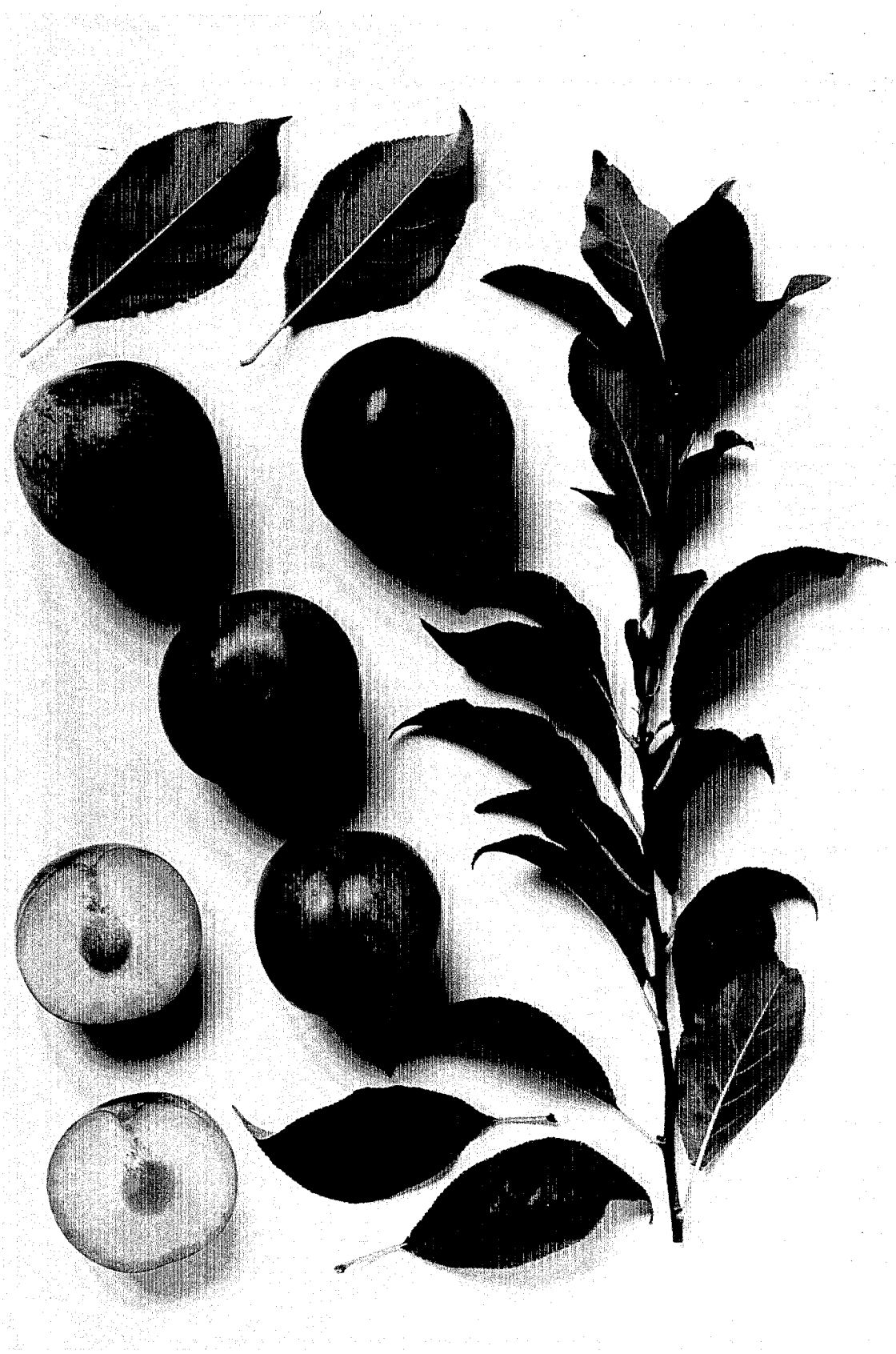

UNITED STATES PATENT AND TRADEMARK OFFICE

CERTIFICATE OF CORRECTION

PATENT NO. : PP 9,513

DATED : April 23, 1996

INVENTOR(S) : Thomas O. Chamberlin, Sr.

It is certified that error appears in the above-identified patent and that said Letters Patent is hereby corrected as shown below:

Column 1, line 19, delete "inclreases" and substitute ---increases---.

Column 1, line 38, between "variety" and "by" insert ---borne---.

Column 2, line 1, delete "has" and substitute ---had---.

Column 2, line 19, delete "and" and substitute ---an---.

Column 3, line 57, delete "as" and substitute ---at---.

Column 4, line 35, delete "3/80" and substitute ---3/8---.

Signed and Sealed this

Twenty-second Day of October, 1996

Bruce Lehman

*Attest:*

BRUCE LEHMAN

*Attesting Officer*

*Commissioner of Patents and Trademarks*